United States Patent
Schamber et al.

(10) Patent No.: US 7,476,858 B2
(45) Date of Patent: Jan. 13, 2009

(54) PARTICLE DETECTION AUDITING SYSTEM AND METHOD

(75) Inventors: Frederick H. Schamber, Murrysville, PA (US); Cornelis G. van Beek, Pittsburgh, PA (US)

(73) Assignee: Aspex Corporation, Delmont, PA (US)

( * ) Notice: Subject to any disclaimer, the term of this patent is extended or adjusted under 35 U.S.C. 154(b) by 253 days.

(21) Appl. No.: 11/584,950

(22) Filed: Oct. 23, 2006

(65) Prior Publication Data

US 2007/0114407 A1 May 24, 2007

Related U.S. Application Data

(60) Provisional application No. 60/729,934, filed on Oct. 26, 2005.

(51) Int. Cl.
*H01J 37/26* (2006.01)
*H01J 37/28* (2006.01)

(52) U.S. Cl. .................. 250/310; 250/306; 250/311; 250/492.2

(58) Field of Classification Search ............... 250/310, 250/311, 306, 492.2
See application file for complete search history.

(56) References Cited

U.S. PATENT DOCUMENTS 5,866,904 A * 2/1999 Todokoro et al. ........... 250/310
5,969,357 A * 10/1999 Todokoro et al. ........... 250/310
6,114,695 A * 9/2000 Todokoro et al. ........... 250/310

OTHER PUBLICATIONS

ENFSI Proficiency Test Program on Identification of GSR by SEM/EDX*; J Forensic Sci. Jul. 2003, vol. 48, No. 4 (online www.astm.org).

* cited by examiner

*Primary Examiner*—Nikita Wells
(74) *Attorney, Agent, or Firm*—Tarolli, Sundheim, Covell & Tummino LLP

(57) ABSTRACT

A system is presented for evaluating the performance of a particle detecting and measuring instrument wherein the instrument receives a specimen and detects the number of particles on the specimen and measures the descriptive parameters of the particles. The system includes a known specimen received by the instrument and wherein the known specimen has known particles on the specimen, with known parameters of each known particle on the specimen. The instrument detects the known particles and measures the parameters thereof. A matching of individual measured particles is made against individual known particles by means of selected known parameters thereof. A comparison is made of the parameters of each measured particle against the parameters of each known particle to which the measured particle was matched and an indication is provided of the instrument's performance as a function of the matching and the comparison.

20 Claims, 1 Drawing Sheet

PARTICLE DETECTION AUDITING SYSTEM AND METHOD

RELATED APPLICATION

This application claims the benefit of U.S. Provisional Patent Application Ser. No. 60/729,934, filed on Oct. 26, 2005, the disclosure of which is entirely incorporated herein by reference.

BACKGROUND OF THE INVENTION

Technical Field

The present invention relates to the art of particle detection instruments and, more particularly, to a system for evaluating the performance of such an instrument and to a specimen having particular use in assessing the performance of the instrument.

Microscope-based particle analyzing systems detect and characterize particles by means of focusing and/or imaging optics. Typical specimens analyzed by such instruments consist of a substrate material on or in which the particles to be analyzed are presented. A difference in brightness (signal level) between the substrate and the particles of interest provides the contrast mechanism which permits the particles to be distinguished from the substrate and permits basic parameters of interest to be extracted, such as the size, shape, and brightness of the particle. Auxiliary capabilities may be provided to measure other particle parameters such as color, thickness, and composition. Two representative types of particle analyzing systems are commonly employed: the light optical microscope (LOM) type employs beams of light for imaging, whereas the Scanning Electron Microscope (SEM) employs a focused beam of electrons. Other varieties of microscope-based particle detection and characterization systems are also possible, based on variations of photon and electron optical systems, as well as scanning mechanical probes, and other types of beams (such as ion beams).

Analysis of particles by means of such microscope-based instruments is preferred for many applications because of the ability to detect very small particles and provide a precise characterization of individual particle size and shape. Microscope-based particle analyzers may also (depending on the nature of the instrumentation) provide valuable compositional information. Lastly, the ability to physically relocate a specific particle for subsequent detailed analysis is important in many applications.

A significant problem related to the use of any particle-measuring instrument is that of assessing its performance for purposes of quality assurance. The problems relate to the small sizes of the particles that are analyzed. Other particle-analyzing instruments (such as flow-type units) cannot reliably measure the small particles which microscope-based instruments can, and thus cannot be used for verification. Microsphere standards that have been developed for testing and calibration of flow-type particle measuring instruments are of limited utility for microscope-based units, and magnification standards available for the checking of manual microscope units are not relevant for checking the automated detection and characterization of particles.

A small number of custom and commercial standards have been fabricated with microscopic particle-like features, with the intent that these be used for checking of automated microscope-based particle analyzing systems. These standards have proven generally unsatisfactory for some or all of the following reasons: (1) the standard is a one-of-a-kind item that cannot be duplicated; (2) the standard does not reasonably simulate the characteristics of a real specimen (e.g., contrast levels are inappropriate or particle locations are too regular); (3) the standard is too fragile or unstable to provide reliable verification of instrument performance over time; (4) the standard does not provide enough particle instances to permit statistically-meaningful assessment of instrument performance; and/or (5) the use of the standard is too difficult or time-consuming to be practical for routine checks. Further, all of the prior-art particle standards suffer from the fact that airborne dust particles and other microscopic contaminants will inevitably be deposited on the specimen with time and use, and thus alter the particle-count and size/shape distribution. In short, until now there has been no particle standard system that has met the need for a sensitive yet practical means of routinely testing the performance of a microscope-based particle analyzing system. Thus, the innovations incorporated in the subject invention represent a significant innovation relative to the field of particle measurements.

Geller MicroAnalytical Laboratory has manufactured a series of Microscope Magnification Standards using semiconductor fabrication techniques to place precise metallic patterns on a quartz substrate (www.gellermicro.com). The patterns are generally designed for pitch measurements, but there is also an array of circular features that are said to be "useful for checking the performance and setup of particle size counting systems." There are several aspects of this specimen that limit its utility as a standard for an automated particle-characterization system. The Geller standard is strictly a physical specimen and does not incorporate a detailed numerical tabulation of individual feature parameters nor does it incorporate a software component to perform the assessment.

The BKA standard is addressed to the needs of a particular application of the SEM type of Automated Particle Analyzing microscope, known as Gun Shot Residue (GSR) analysis. GSR analysis is concerned with detecting and identifying particles with a characteristic composition of lead, barium, and antimony (Pb/Ba/Sb) that are known to be produced by the discharge of a firearm, and is a widely used form of criminal forensic evidence. The standard was developed by Dr. Ludwig Niewohner at the Bundeskriminalamt (BKA), the German federal police bureau roughly equivalent to the American FBI. It is known by its inventor as the SPS (several models) but will here be referred to as the BKA Standard. It was originally developed to serve the need for a robust replicable standard for inter-laboratory comparisons but is also commercially available.

The BKA Standard is constructed using semiconductor-type microfabrication techniques. A German Patent (DE 199 32 357 C2) was issued regarding the method of construction of this physical specimen. Said patent (BKA PATENT) is a broadly stated disclosure relative to the general use of semiconductor microfabrication techniques for construction of a particle specimen.

The BKA PATENT deals with the specific technique used to fabricate a physical specimen, whereas the subject invention deals with a system used for performance checking.

The BKA Standard, is addressed to a more specific application than the subject invention. Like the physical component of the subject invention, the BKA Standard is constructed so as to provide a plurality of particle-like features at fixed locations on the specimen and of several size ranges. The detection and characterization of these known particle-like features provides a measure of the performance of an Automated Particle Analyzing Microscope. However, the BKA Standard is simply a physical specimen, rather than a system. As such, it does not incorporate nor does its published use teach the detailed numerical tabulation of individual feature parameters, nor does it incorporate a software component to perform the assessment of performance. The BKA Standard also does not incorporate any kind of analysis or reporting functionality, and therefore although it may be usefully employed in a procedure to produce an indication of instrument performance, it does not itself produce such an indication.

An important functional distinction between the BKA Standard and the subject invention is that the BKA Standard can be described as a particle-class-count standard. That is, the measure of the performance of an Automated Particle Analyzing Microscope via the BKA Standard is the number of particles reported in each of the known particle size classes (see example in reference 1). Unlike the BKA Standard, the subject invention can be described as a particle-instance standard system. That is, the assessment is based on the degree of agreement between each individual particle instance measured and the known parameters of that same particle.

The BKA Standard is not accompanied by a detailed numerical tabulation of known particle parameters. Rather, the BKA Standard is accompanied by a low-resolution graphical representation (map) of the location of each size-class of particle on the specimen. This graphical representation is suitable only for gross identification purposes, and does not provide detailed numerical information.

One of the key issues addressed by the subject invention is the ability to distinguish foreign particulate material accidentally deposited on the specimen, from the "known" particles intentionally fabricated on the specimen. The operating instructions for the BKA Standard describe the use of the afore-mentioned graphical "map" as a means for ascertaining whether a reported particle is indeed a known (fabricated) particle. This is described as strictly a visual comparison however (specifically, the overlaying of a transparency copy of the map over a plot of measured particle locations), and besides being different in the method of implementation, is vastly inferior in convenience, reliability, and precision to the numerical particle matching disclosed in the subject invention.

The BKA Standard does not provide detailed performance metrics (e.g., instrument magnification) from the comparison of measured particle parameters to known particle parameters.

SUMMARY OF THE INVENTION

In accordance with one aspect of the present invention, a system is provided for evaluating the performance of a particle detecting and measuring instrument wherein the instrument receives a specimen and detects the number of particles on the specimen and measures the descriptive parameters of the particles. The system includes a known specimen received by the instrument and wherein the known specimen has known particles on the specimen with known parameters of each known particle on the specimen. The instrument detects the known particles and measures the parameters thereof. A matching takes place of individual measured particles against individual known particles by means of the known parameters thereof. A comparison is made of the parameters of each measured particle against the parameters of the known particle to which the measured particle is matched. An indication is provided of the instrument's performance as a function of the matching and the comparison.

In accordance with another aspect of the present invention, a synthetic particle specimen is provided containing a plurality of known particles on a synthetic substrate. This substrate is constructed of a material whose average atomic number approximates the average atomic number of an actual substrate on which actual particles are collected and mounted. The synthetic substrate is constructed from a polymer resin that has been deposited on a stable base material. The synthetic substrate material is a BCB polymer. The stable base material is silicon and the synthetic main particles are fabricated from materials whose elemental composition is chosen to match the elemental composition of actual particles of interest relative to an application.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Figure 1:
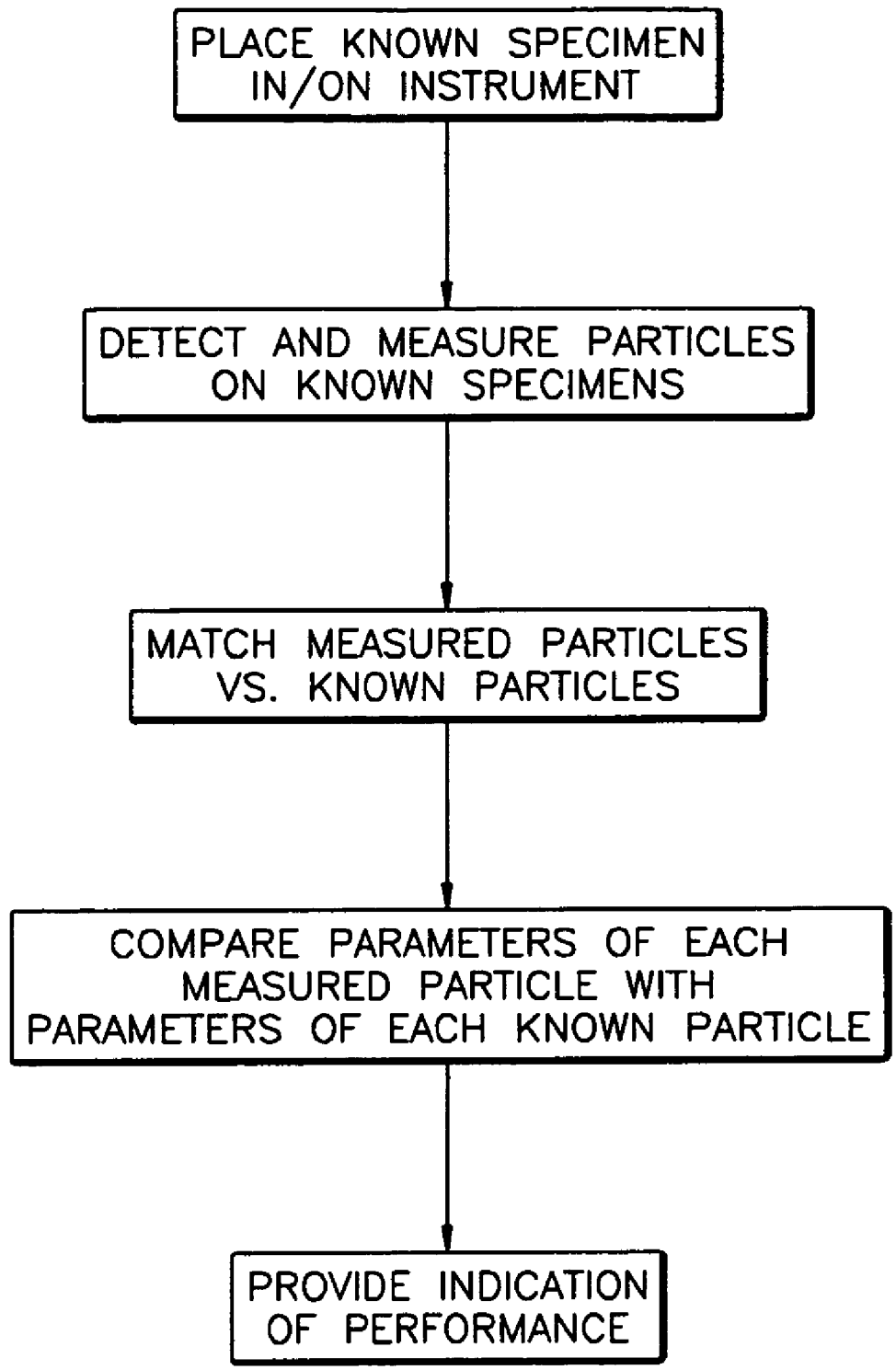
FIG. 1 illustrating a flowchart that is helpful in understanding the invention.

The subject invention relates generally to a method of assessing the performance of an existing type of instrument, here termed an Automated Particle Analyzing Microscope and, more particularly to the use of a novel Synthetic Particle Specimen (SPS) enabling said method to be carried out automatedly in an improved manner. The invention makes use of said Synthetic Particle Specimen which is implemented as a system incorporating a physical specimen with innovative design elements, documented with a detailed numerical representation of its large number of Synthetic Particle features, and accompanied by computer software which automates the assessment. The Synthetic Particles are fabricated on said physical SPS member at known locations which simulate the random spatial distribution of Actual Particles collected on the surface of an Actual Particle Specimen. Said Synthetic Particles may also be fabricated with variations in size, shape, and composition which again simulate the random distribution of these same parameters for Actual Particles present on an Actual Particle Specimen. In use, the physical component of the Synthetic Particle Specimen is placed in the Automated Particle Analyzing Microscope and an analysis is performed in the normal manner as would be used to analyze Actual Particles present on an Actual Particle Specimen. This analysis results in a listing of detected Particles and their measured parameters, such as location, size, shape and composition. Said accompanying software component of the SPS completes the assessment by performing a fully automated matching and comparison between the listing of measured Particles and their parameters versus the known Synthetic Particles and their parameters as documented in said detailed numerical representation of said Synthetic Particle features. From this comparison, the software program extracts and reports a numerical analysis of the Automated Particle Analyzing Microscope's performance. The foregoing is illustrated in FIG. 1.

DEFINITIONS

Particle—A small discrete material entity including micron-scale size solid fragments.

Specimen Substrate—A surface on which Particles are collected or placed for analysis. For example, a filter paper used for collection of Particles or a sticky tape onto which Particles are transferred are typical specimen substrates.

Particle Specimen—A Specimen Substrate on or in which Particles have been collected or placed for analysis.

Actual Particle/Actual Specimen/Actual Substrate

The term Actual is used to designate the normal material entity as might be utilized or of interest in an actual application. For example, an Actual Specimen might be prepared by passing a fluid through a filter paper prior to analyzing the filter-paper specimen (Actual Specimen) for the presence of contamination particles (Actual Particles) deposited on said filter paper (Actual Substrate).

Automated Particle Analyzing Microscope—An automated (e.g. computer-controlled) instrument employing microscopic imaging means to assess the quantity and properties of Particles present on a Particle Specimen. An automated Scanning Electron Microscope (SEM) or an automated Light Optical Microscope (LOM) are both considered to be representative types of said Automated Particle Analyzing Microscope.

Synthetic Particle Specimen—A specimen specifically fabricated or chosen to simulate an Actual Particle specimen.

Synthetic Substrate—A surface specifically fabricated or chosen to simulate one or more relevant properties of an Actual Specimen Substrate. A Synthetic Substrate may be a discrete body of material or a coating applied over a base material.

Synthetic Particle—A feature fabricated on or in a Synthetic Substrate for purposes of simulating relevant characteristics of an Actual Particle. A Synthetic Particle will typically differ from an Actual Particle in that it is permanently affixed to the Synthetic Substrate either via direct fabrication on said Synthetic Substrate or by employing some means of affixing separately fabricated said Synthetic Particles to said Synthetic Substrate (e.g., via a mounting medium or fixative).

MEMS—This term is here used in a generic sense to encompass the various techniques that have been used to create microscopic structures using the three basic microfabrication building blocks of deposition, lithography and etching. An overall reference to the topic may be found at: www-.memsnet.org/mems/. In said respect the MEMS technology can employ substantially the same techniques as those used within the semiconductor industry to construct electronic devices and these can be considered equivalent technologies for purposes of this document.

Particle Fabrication Pass—The sequence of MEMS steps necessary to fabricate on the Synthetic Substrate one or more Synthetic Particles of particular material and particular thickness. A multiplicity of Particles with a multiplicity of two-dimensional shapes may be fabricated in a Particle Fabrication Pass, but they may all be of the same material (e.g. aluminum metal) and thickness (e.g. 0.25 micron) per the limitations of the MEMS processes being employed.

Average Atomic Number—The mean atomic number of a material based on the quantity and atomic number (Z) of each of the constituent atoms. Example: the average atomic number of $H_2O$ is 3.33 (2 hydrogen atoms with Z=1, 1 oxygen atom with Z=8, average =[1+1+8]/3).

This invention pertains to a system for verifying the performance of an Automated Particle Analyzing Microscope by use of a novel Synthetic Particle Specimen and a novel method that employs said SPS member. The SPS is a system comprised of a physical specimen member, an accompanying numerical representation of said physical member, and a software component which automatically performs the assessment of the performance of said Automated Particle Analyzing Microscope. In a representative embodiment, said physical specimen member can be constructed by depositing a uniform layer of BCB polymer resin on a silicon wafer which is then cured to form a stable layer. On top of this Synthetic Substrate is then deposited a multiplicity of Synthetic Particles using conventional MEMS techniques, involving steps of material deposition, photolithography and etching as required. MEMS techniques represent a highly effective means of creating precise two-dimensional shapes of small size and arbitrary shape complexity with a third thickness dimension that can also be precisely controlled. By using a series of Particle Fabrication Passes involving deposition of differing shapes, differing thicknesses and differing materials, a collection of Synthetic Particles may be created on the physical Synthetic Particle Specimen member which collection simulates a wide variety of Actual Particles.

An important aspect of the novelty and utility of the invention relates to the management of atomic number contrast. When Actual Particle Specimens are analyzed in an Automated Particle Analyzing Microscope of the SEM type, the Particles are typically distinguished from the substrate by means of the signal obtained from a Back-Scattered Electron (BSE) detector. As is well known, the intensity of the BSE signal varies in a regular manner according to the Average Atomic Number of the material being analyzed. Thus, Actual Particles whose Average Atomic Number is greater than the Average Atomic Number of the Actual Substrate may be distinguished from said Substrate by their stronger (brighter) signal, and the reliability with which said Actual Particles can be detected and measured on said Actual Substrate is thus strongly dependent on the specific Average Atomic Numbers of said Particle and said Substrate. Consequently, it is an important aspect of the novelty and utility of this invention in that it embodies means to accurately simulate the average atomic numbers of Actual Particles residing on Actual Substrates. In particular it is the practice of this invention to utilize appropriately thin layers of a first material deposited over a second material so that the BSE signal obtained is a mixture of the signals from the first and second materials, due to the penetrating range of the electron beam. In this manner, the BSE signal of materials of arbitrary Average Atomic Number can be simulated.

A first embodiment of said described physical specimen member is depicted above. A first embodiment was constructed with a single Particle Fabrication Pass and thus the Synthetic Particles produced were all of the same material (aluminum metal) and thickness (approximately ½ micron). Other SPS member constructions are contemplated, however, including utilization of additional Particle Fabrication Passes to create Synthetic Particles with a greater variety of materials and thickness. The provision of Particles of different and varying composition is anticipated, both to simulate a broader range of Average Atomic Number, and to verify the performance of the x-ray spectrometer and its associated material classification algorithms. An ideal SPS member will simulate both the Average Atomic Number of the Actual Substrate and the distribution of Average Atomic Numbers of the Actual Particles being detected.

A very important aspect of the novelty and utility of the present SPS member is that each Synthetic Particle fabricated on the surface of the said physical SPS specimen member is documented in a numerical tabulation. Subsequent to the analysis of the physical SPS member by an Automated Particle Analyzing Microscope, this numerical tabulation permits precise numerical comparison of each measured Synthetic Particle parameter against the corresponding known parameter for that Synthetic Particle feature. The provided parameters include, at present, the X, Y position coordinates, the average diameter, the aspect ratio, and the particle type classification (indicative of material and thickness) of each Synthetic Particle. Other important parameters that may be provided (as appropriate) in future implementations include additional parameters related to particle shape, thickness, and composition. In a preferred implementation of the SPS member, the numerical parameters of the SPS member are tabulated in the form of a spreadsheet file, thus making it easy to produce graphs and perform comparisons with these parameters.

The detailed numerical tabulation of known particles and their descriptive parameters is a key provision relative to two of the most significant aspects of the invention. Firstly, the detailed tabulation of known particles and parameters permits measured particles to be unambiguously matched to specific known particles. Foreign material will not be matched, however, and will thus not distort the performance assessment. Secondly, the precisely known parameters of the known particles permit the extraction of a number of performance metrics of the Automated Particle Analyzing microscope that are not available by class-count standards. Because the parameters of each particle are precisely known, a comparison of the measured and the known parameters permits measurement errors to be quantified by suitable metrics. For example, systematic differences in measured particle location can be analyzed to achieve a measure of said microscope's deviation from intended magnification.

A further useful aspect of the present invention is the implementation of a software component to facilitate the comparison of the measured Particle parameters against the known Synthetic Particle Parameters provided in the numerical tabulation. This software component enables a superior numerical comparison to be automatedly made between the detected Synthetic Particles and the numerically tabulated Synthetic Particle parameters of the SPS member. In the present embodiment, the numeric data parameters for said Synthetic Particles are pre-stored as tables in a spreadsheet. The Excel spreadsheet is further augmented by the embedding of computer code which computer code comprises a completely automated software program for matching and comparing measured Particle parameters obtained from analysis of the physical SPS specimen with said pre-stored parameters. When used for checking the performance of an Automated Particle Analyzing Microscope, the operator of said Automated Particle Analyzing Microscope first analyzes the physical SPS specimen member employing the normal analytical capabilities of said Automated Particle Analyzing Microscope, and producing a computer file containing the numerical results of said analysis. The operator then activates the software component of the SPS member to evaluate the analysis results contained in said computer file, by comparing the measured particle parameters in said computer file against the tabulated numerical parameters of the SPS member. Such representative comparison typically involves the automated sequential steps of reading-in the already measured Synthetic Particle data, transforming said measured particle data location coordinates to achieve approximate registration with the numerically tabulated Synthetic Particle coordinates, matching each Synthetic Particle feature to its corresponding measured Particle datum as possible, systematically refining the transformation parameters to achieve an optional fit between the coordinates of known Synthetic Particles and their measured counterparts, and producing a report that summarizes various performance metrics, such as number of missed particles by size, number of extraneous particles by size, magnification error of the measuring instrument and mean end standard deviation of the discrepancies found between known and measured particles sizes. A complete particle analysis conducted automatedly in the foregoing manner can be performed both easily and quickly by a minimally-trained operator, and produces a detailed, precise, and reliable assessment of instrument performance. If compositional characterization for the particles being analyzed forms part of the automated analysis, such as in the case of x-ray analysis by an Automated Particle Analyzing Microscope of the SEM type, then such measurements can be added to the read-in data of the present method.

The above describes a novel and highly useful invention for use in evaluating the performance of an Automated Particle Analyzing Microscope. It will be recognized that the salient features of the invention incorporate three significant components: (1) a physical Synthetic Particle Specimen of novel design and construction; (2) a numerical tabulation of the parameters of said Synthetic Particle Specimen; and (3) a method of using the first two components in a systematic manner, as may be embodied in a computer program, so as to facilitate a comprehensive yet convenient test of said Automated Particle Analyzing Microscope.

It is further contemplated that still other constructions for the presently disclosed SPS member can be devised by persons skilled in this field than herein described without departing from the spirit and scope of this invention. It is still further contemplated that the presently disclosed SPS member can also be employed to audit the performance of related automated particle detection instruments other than the presently disclosed Automated Particle Analyzing Microscope.

Although the foregoing has been described in conjunction with a preferred embodiment, it is to be appreciated that various modifications may be made without departing from the spirit and scope of the invention as defined by the appended claims.

We claim:

1. A system for evaluating the performance of a particle detecting and measuring instrument wherein said instrument receives a specimen and detects the number of particles on said specimen and measures the descriptive parameters of said particles, said system comprising:
   a known specimen received by said instrument and wherein said known specimen has known particles on said specimen, with known parameters of each said known particle on said specimen;
   said instrument detecting said known particles and measuring the parameters thereof;
   a matching of individual said measured particles against individual said known particles by means of selected known parameters thereof;
   a comparison of said parameters of each said measured particle against said parameters of said known particle to which said measured particle was matched; and
   an indication provided of said instrument's performance as a function of said matching and said comparison.

2. A system as set forth in claim 1 wherein said known parameters of each said known particle on said known specimen are presented in a numeric tabulation.

3. A system as set forth in claim 2 wherein said numeric tabulation is in the form of a computer-readable file.

4. A system as set forth in claim 2 wherein said numeric tabulation is incorporated in a computer program.

5. A system as set forth in claim 2 wherein said numeric tabulation of parameters includes at least one measure of each said known particle size or shape.

6. A system as set forth in claim 2 wherein said numeric tabulation of known parameters includes the spatial position coordinates of each said known particle.

7. A system as set forth in claim 2 wherein said numeric tabulation of parameters includes a measure of the thickness of each said known particle.

8. A system as set forth in claim 2 wherein said numeric tabulation of parameters includes a measure of the composition or material type of each said known particle.

9. A system as set forth in claim 2 wherein said numeric tabulation of known particle parameters may be edited to designate or eliminate sites at which said known particle features may be missing or defective.

10. A system as set forth in claim 2 wherein said numeric tabulation of known particle parameters may be edited to add sites at which extraneous particle-like features are physically present.

11. A system as set forth in claim 1 wherein said specimen is provided on a synthetic substrate which is constructed of a material whose average atomic number approximates the average atomic number of an actual substrate on which actual particles may be collected or mounted for analysis.

12. A system as set forth in claim 11 wherein said synthetic substrate material is a polymer resin that has been deposited on a stable base material.

13. A system as set forth in claim 12 wherein said stable base material is silicon.

14. A system as set forth in claim 1 wherein said known particles are fabricated from aluminum metal.

15. A system as set forth in claim 1 wherein said known particles are fabricated from a plurality of materials.

16. A system as forth in claim 1 wherein said known particles are fabricated as sufficiently thin layers of material so as to be partially transparent to the analyzing beam employed by said particle detecting and measuring instrument.

17. A system as set forth in claim 1 wherein said matching of said measured particles to said known particles, said comparison of said measured particle parameters to said known particle parameters, and said indication of said instrument's performance as a function of said matching and said comparison are conducted automatedly by means of a digital computer.

18. A synthetic particle specimen containing a plurality of known particles on a synthetic substrate comprising:
    said substrate being constructed of a material whose average atomic number approximates the average atomic number of an actual substrate on which actual particles are collected or mounted; and
    said known particles being constructed of sufficiently thin material to allow partial penetration by an electron beam employed by an Automated Particle Analyzing Microscope of the SEM type.

19. A specimen as set forth in claim 18 wherein said particles are fabricated from aluminum metal.

20. A specimen as set forth in claim 18 wherein said substrate is a cured polymer material deposited on silicon.

* * * * *